(12) United States Patent
Perryman et al.

(10) Patent No.: US 9,731,140 B1
(45) Date of Patent: Aug. 15, 2017

(54) CONTROLLER INTERFACE FOR AN IMPLANTABLE STIMULATOR DEVICE

(71) Applicant: Micron Devices LLC, Miami Beach, FL (US)

(72) Inventors: Laura Tyler Perryman, Miami Beach, FL (US); Chad David Andresen, Miami Beach, FL (US)

(73) Assignee: Micron Devices LLC, Miami Beach, FL (US)

( * ) Notice: Subject to any disclaimer, the term of this patent is extended or adjusted under 35 U.S.C. 154(b) by 0 days.

(21) Appl. No.: 14/952,302

(22) Filed: Nov. 25, 2015

Related U.S. Application Data

(60) Provisional application No. 62/084,743, filed on Nov. 26, 2014.

(51) Int. Cl.
*A61N 1/00* (2006.01)
*A61N 1/372* (2006.01)

(52) U.S. Cl.
CPC ..... *A61N 1/37247* (2013.01); *A61N 1/37264* (2013.01)

(58) Field of Classification Search
CPC .......................... A61N 1/37247; A61N 1/37264
See application file for complete search history.

(56) References Cited

U.S. PATENT DOCUMENTS

2009/0118780 A1* 5/2009 DiLorenzo ......... A61N 1/37247
607/2

* cited by examiner

Primary Examiner — George Manuel
(74) Attorney, Agent, or Firm — Fish & Richardson P.C.

(57) ABSTRACT

Some computer-assisted methods include: presenting configuration options to a user of the implanted stimulator device, the configuration options comprising stimulation parameters for the implanted stimulator; receiving a user specification of the configuration options in response to the presented configuration options; receiving user feedback when the user specified configuration options are implemented at the implanted stimulator device, the user feedback comprising a quantitative index of pain resulting from implementing the user specified configuration options on the implanted stimulator device; building a user profile for the user based on the user specified configuration options and the user feedback, the user profile including the user specified configuration options as well as the corresponding quantitative index of pain; and selecting at least one configuration option based on the user profile when the configuration options are subsequently presented to the user for a later treatment.

18 Claims, 12 Drawing Sheets

CONTROLLER INTERFACE FOR AN IMPLANTABLE STIMULATOR DEVICE

CROSS-REFERENCE TO RELATED APPLICATIONS

This application claims the benefit of and priority of U.S. Provisional Patent Application No. 62/084,743, which was filed on Nov. 26, 2014. The contents of the foregoing U.S. provisional application is incorporated by reference herein in its entirety.

TECHNICAL FIELD

This application relates generally to implantable stimulator devices.

BACKGROUND

Active implanted stimulation devices have been utilized for both subcutaneous treatments as well as deeper applications such as pacing, defibrillation, spinal and gastric stimulation.

SUMMARY

In one aspect, some implementations provide a computer-assisted method to configure settings on an implanted stimulator device. The method includes: presenting configuration options to a user of the implanted stimulator device, the configuration options including stimulation parameters for the implanted stimulator; receiving a user specification of the configuration options in response to the presented configuration options; receiving user feedback when the user specified configuration options are implemented at the implanted stimulator device, the user feedback including a quantitative index of pain resulting from implementing the user specified configuration options on the implanted stimulator device; building a user profile for the user based on the user specified configuration options and the user feedback, the user profile including the user specified configuration options as well as the corresponding quantitative index of pain; and selecting at least one configuration option based on the user profile when the configuration options are subsequently presented to the user for a later treatment.

Implementations may include one or more of the following features.

The stimulation parameters may include polarity setting such that presenting configuration options to the user of the implanted stimulator device includes presenting configuration options that include a polarity setting of each electrode of the implanted stimulator device. Building a user profile for the user includes building a user profile that includes the polarity setting of each electrode that gives rise to the corresponding quantitative index of pain. Selecting at least one configuration option may include selecting a polarity setting for at least one of the electrodes of the implanted stimulator device.

The stimulation parameters may include pulse rate, pulse width, and pulse amplitude such that presenting configuration options includes presenting configuration options that that include pulse rate, pulse width, and pulse amplitude. The method may further include, in response to determining that the quantitative index of pain is above a threshold level, prompting the user to change the configuration options. Prompting the user to change the configuration options may include presenting at least one configuration option based on the user profile. The method may further include: increasing, by an amount that is proportional to the quantitative index of pain, a pulse amplitude of stimulation pulses for application at a particular electrode. The method may further include: in response to determining that the quantitative index of pain is below a threshold level, prompting the user to reduce stimulation. Prompting the user to reduce stimulation may include prompting the user to reduce stimulation by decreasing a pulse amplitude of stimulation pulses for application at a particular electrode. Presenting configuration options may further include cycling through the each configuration option subject to user adjustment, the configuration options including a polarity setting of each electrode of the implanted stimulator device as well as pulse parameters of stimulation pulses for application at a particular electrode.

Building a user profile may further include recording an adjustment in a configuration option made by the user that results in an improved quantitative index of pain. Recording the adjustment in the configuration option may include recording an adjustment in a pulse parameter or a polarity setting.

Some implementations provide a controller device to configure settings on an implanted stimulator device. The controller device includes a processor configured to perform the operations of: presenting configuration options to a user of the implanted stimulator device, the configuration options including stimulation parameters for the implanted stimulator; receiving a user specification of the configuration options in response to the presented configuration options; receiving user feedback when the user specified configuration options are implemented at the implanted stimulator device, the user feedback including a quantitative index of pain resulting from implementing the user specified configuration options on the implanted stimulator device; building a user profile for the user based on the user specified configuration options and the user feedback, the user profile including the user specified configuration options as well as the corresponding quantitative index of pain; and selecting at least one configuration option based on the user profile when the configuration options are subsequently presented to the user for a later treatment.

Implementations may include one or more of the following features.

The stimulation parameters may include polarity setting such that presenting configuration options to the user of the implanted stimulator device includes presenting configuration options that include a polarity setting of each electrode of the implanted stimulator device. Building a user profile for the user may include building a user profile that includes the polarity setting of each electrode that gives rise to the corresponding quantitative index of pain. Selecting at least one configuration option may further include selecting a polarity setting for at least one of the electrodes of the implanted stimulator device.

The stimulation parameters include pulse rate, pulse width, and pulse amplitude such that presenting configuration options includes presenting configuration options that that include pulse rate, pulse width, and pulse amplitude. The operations may further include: in response to determining that the quantitative index of pain is above a threshold level, prompting the user to change the configuration options. The operations may further include: further including in response to determining that the quantitative index of pain is below a threshold level, prompting the user to reduce stimulation.

The details of one or more implementations are set forth in the accompanying drawings and the description below.

Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
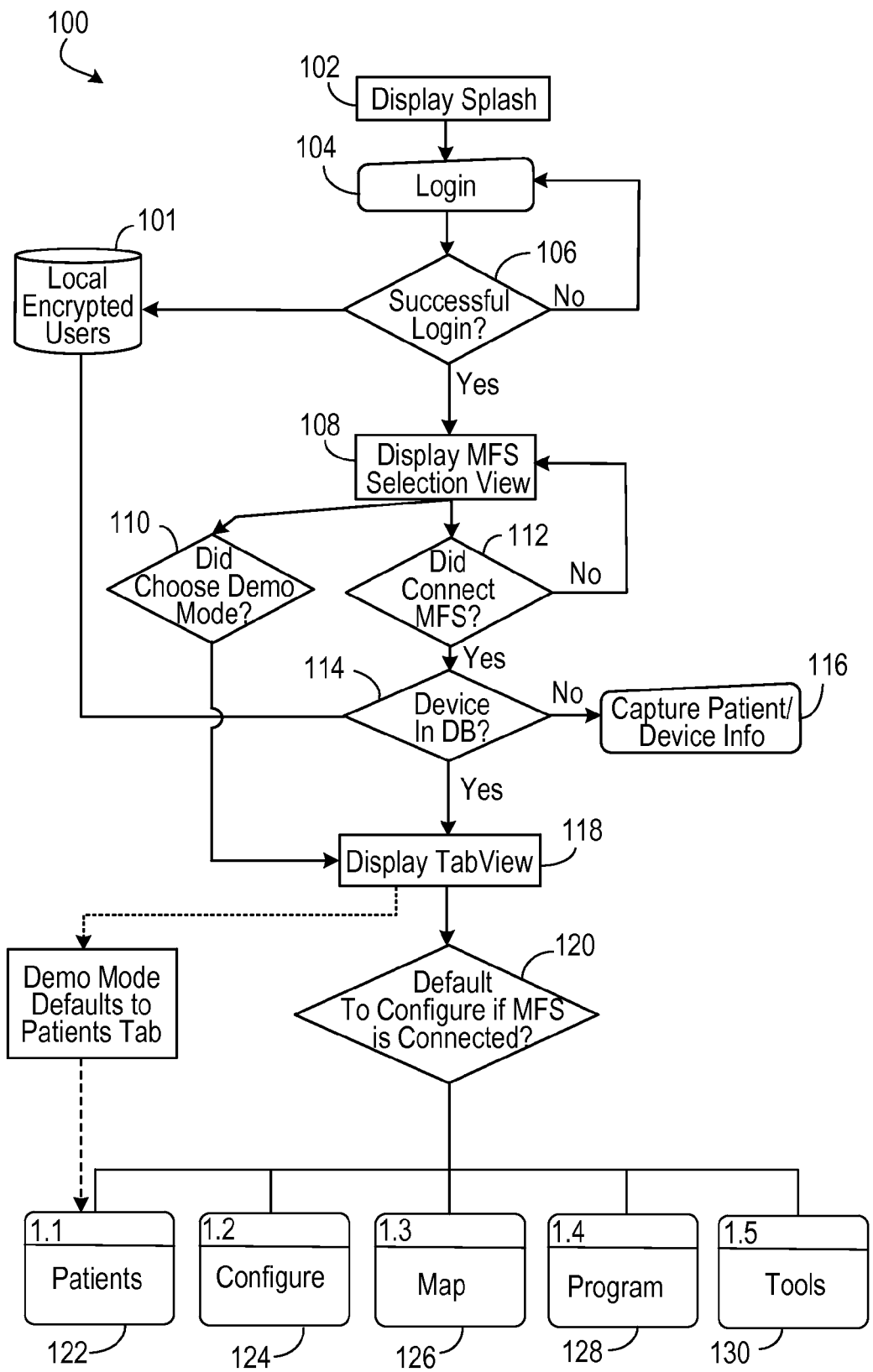
FIG. 1 is a flow chart of an example of a process for interacting with an implanted stimulator device.

In various implementations, systems and methods allow a user to configure stimulation settings of an implanted stimulation device wirelessly powered by an external controller device. Notably, the implanted stimulator device does not include a battery or inductive coupling. Instead, the implanted stimulator device contains the circuitry necessary to receive the pulse instructions from the external controller outside the body. For example, various implementations employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil. Moreover, the implanted stimulator device includes one or more electrodes and one or more conductive antennas (for example, dipole or patch antennas), and internal circuitry for frequency waveform and electrical energy rectification. In some implementations, the polarity of the electrodes (or each electrode pair) of the implanted stimulator device can be configured at a controller device, along with other simulation parameters such as waveform, duration, pulse width, and pulse repetition rate. Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

In these implementations, a user interface is provided for the external controller device to register an implanted stimulator device. The user interface also allows a patient to configure stimulation settings to be effectuated on the implantable stimulator device. The stimulation settings include polarity settings at each electrode and pulse parameters for the stimulating current. In particular, some implementations collect user feedback reflecting pain relief resulting from various combination of stimulation parameters. Such feedback may be assembled to build a knowledge database, like an expert system. The knowledge database may be subsequently leveraged to guide the patient, or other patients, in configuring stimulation parameters including, for example, the polarity settings at each electrode or electrode pair.

In some cases, a software application may incorporate a unique learning engine which uses the history of stimulation parameter adjustments made by the patient and resulting patient reported pain level scores to determine a combination of future parameter settings that can be used to provide improved pain relief for which the patient may prefer based on his/her historical usage patterns and positions. In some instances, the stimulation parameters include, for example, pulse current, pulse width, pulse rate, dosage time, and electrode polarity patterns.

By way of illustration, the learning engine may determine recommended stimulation parameter settings based on variables such as patient age, patient gender, target nerve, depth of implantation, type of implanted stimulator devices, anatomic position, duration of therapy, time of day, prior stimulation parameter settings (for example, prior pulse current, pulse amplitude (or transmit power), pulse width, pulse rate, or electrode polarity), and/or patient pain levels corresponding to prior stimulation parameters. For example, each time after an adjustment of parameters, the user can record his/her level of pain using a numeric pain intensity scale presented by the software application. Based on the recorded pain level and corresponding parameter adjustments, as well as other variables such as those described above, the learning engine may build a profile including the combination of parameters that gives rise to improved therapeutic pain relief. The learning engine may then be applied in various approaches. In one implementation, after the user has built up history for their profile, the software application may proceed to offer an "Auto" mode on the front page of the Configure tab that can enable the user to actively change the stimulation parameters. In another implementation, after the user records his/her present pain rating on the numeric pain intensity scale, the application offers to automate setting a parameter or parameters which are calculated by leveraging historical user input. In yet another implementation, a "Build Your Stim Profile" section of the software application may enable the user to rank the effectiveness of therapy through visual analog scale, numeric pain intensity scale, or binary (yes or no). While in the "Build Your Stim Profile" mode, the software application may begin to cycle through calculated settings and learn the user's preferences. In this cycling process, the application can build a profile more quickly. The feature of the learning engine and its automated parameter selection criteria can offer the user a simplified form of interaction which can be daunting when juggling the many variables involved with stimulation parameters.

FIG. 1 is a flow chart 100 of an example of a process for a user to interact with an implanted stimulator device. The process may be implemented by software installed on an external controller device in direct or indirect communication with an implantable stimulator device. Example external controller devices can include a portable computing device, such as a tablet, a handheld device, or a laptop device. In some implementations, the external controller device has its own power supply, for example, a battery pack. The external controller device may be separate from or part of a microwave field stimulator (MFS) that is in communication with and providing power to the implantable stimulator device. If the external controller is separate from the MFS, the external controller may communicate with the MFS during operation such that the MFS is programmed according to the instructions from the mobile computing device. The communication may be in the form of a cabled communication (e.g., USB connection) or a wireless communication (e.g., based on Bluetooth and IEEE 801.11).

Figure 2A:
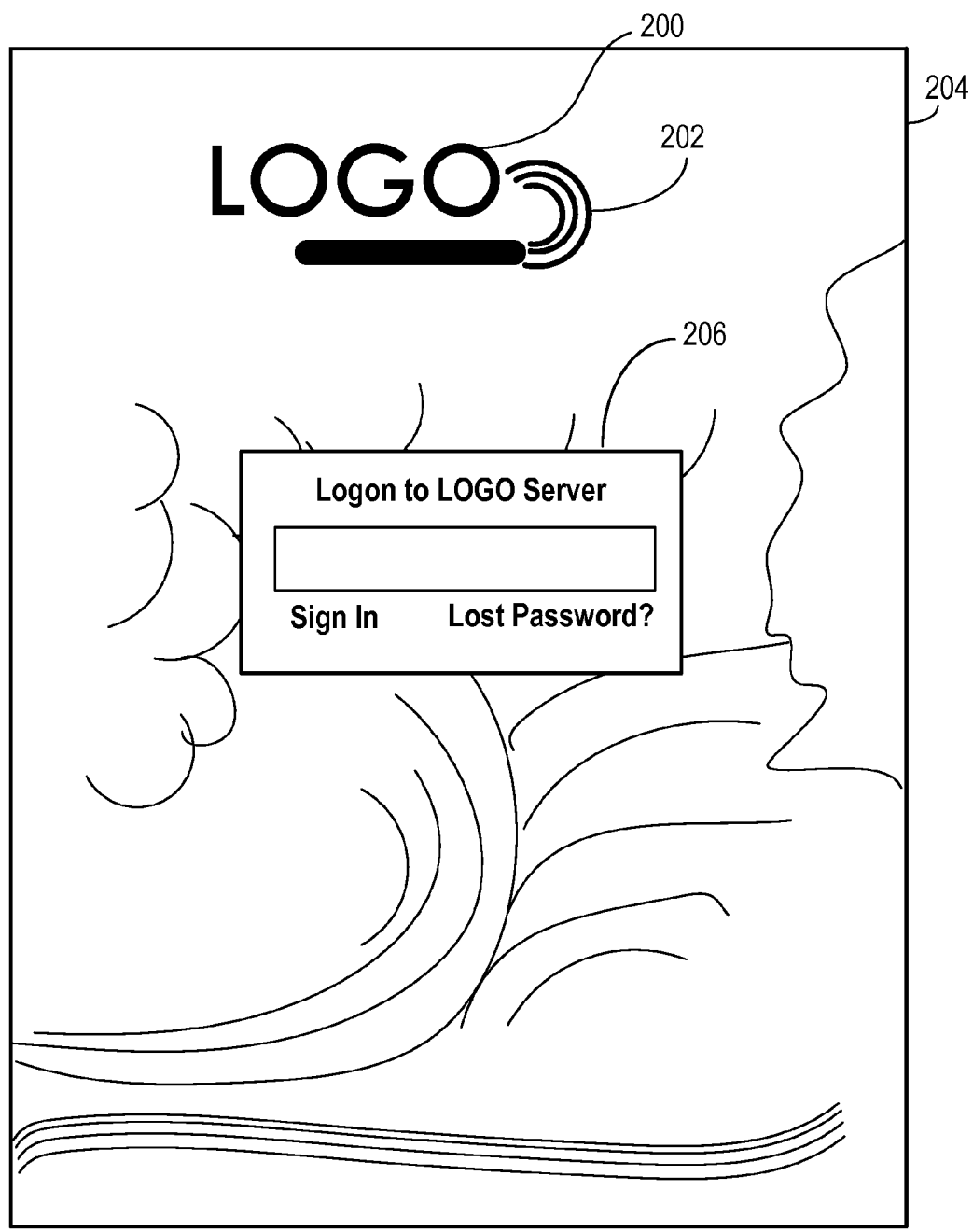
FIG. 2A through 2F are illustrations of examples of user interfaces.

As shown in flow chart 100, a logo is displayed to identify the application program invoked (102). An example logo display 202 is shown in FIG. 2A. The logo may be displayed along with a background image 204. This example further shows a login window 206 as a mechanism to enforce access control.

Returning to FIG. 1, in one instance, a user enters a valid user name and password before the user can login (104) to access the controller and configure the stimulation parameters. In this instance, the login attempt is first authenticated to determine success (106). If the login attempt is not successful, the flow will proceed back to display the login window. If the login attempt is successful, the process will proceed to display a microwave field stimulator (MFS) selection view (108) and grant access to database 101. Database 101 may include encrypted data encoding past stimulation parameters and patient feedback. In other words, only registered user with a valid password entry may obtain access in order to configure the stimulation parameters. Thus, such access control enforces security features of configuring stimulation parameters are tailored to a particular patient.

In some implementations, additional system level checks may be performed before the user may configure stimulation parameters. In one instance, a determination is made regarding whether a microwave field stimulator (MFS) is connected to an implanted stimulator device (112). The work flow may proceed when the MFS is in communication with an implanted stimulator. In some cases, the MFS is wirelessly connected to the implanted stimulator through electrical radiative coupling (e.g., through the electromagnetic midfield) and not inductive coupling. If the MFS is connected to an implanted stimulator device, another determination is made regarding whether the connected stimulator device is in the database 101 containing recorded stimulation parameters (114). If the connected stimulator device is not in the database 101, the work flow may then proceed to capture patient/device information and register the captured information in the database. In some instances, a determination is made regarding whether the controller is operating in a demo mode (110). For context, demo mode allows the software to showcase the features and controls available to the user without effectuating such features on the physical MFS unit itself.

After successful login and verifications, a TabView may be displayed in some implantations (118). The TabView may allow a user to choose a view (120). Some implementations may provide five views, namely, patient view 122, configure view 124, map view 126, program view 128, and tools view 130. In one implementation, the default mode is the patient view 122. In another implementation, the chosen view is the configure view 124 by default.

Figure 2B:
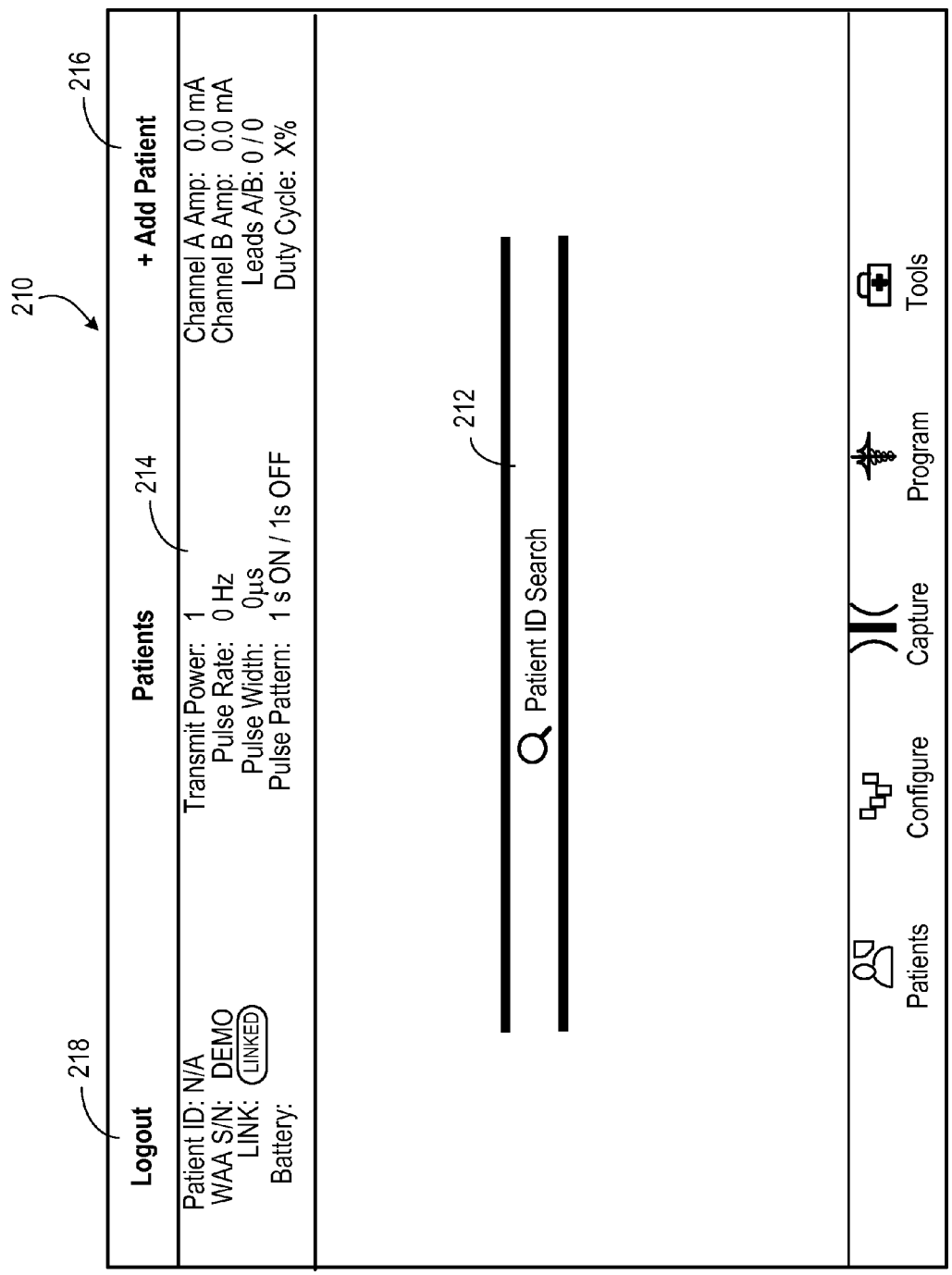

Referring to FIG. 2B, an example user interface 210 is displayed for patient view 122. Through search panel 212, a user may look for a particular patient's profile in the database. Generally, patient profile information 214 is only accessible to authorized users such as the patient himself/herself, his/her attending physician, his/her appointed nurse or caregiver. Such profile information may also be anonymized to preserve patient privacy information. For example, in some instances, only a patient ID is displayed. In these instances, patient profile information may include wearable antenna assembly (WAA) signal/noise (S/N), link status, battery status, transmit power status, pulse rate, pulse width, pulse pattern, duty cycle, current amplitude for each channel of the each implanted stimulator. Such profile information may correspond to the profile information as last accessed. In some instances, the WAA can be an MFS device. In some instances, the WAA may be a relay module that bridges signal transmission between an MFS and an implanted stimulator device. When configured as a relay module, the WAA may include a battery or other power source. The WAA may also be a passive device without an on-board battery or other power source. Generally, such profile information varies from patient to patient. Tab 216 may allow an additional patient to be added to the database. Tab 218 may allow the logged-in user to log out.

Figure 2C:
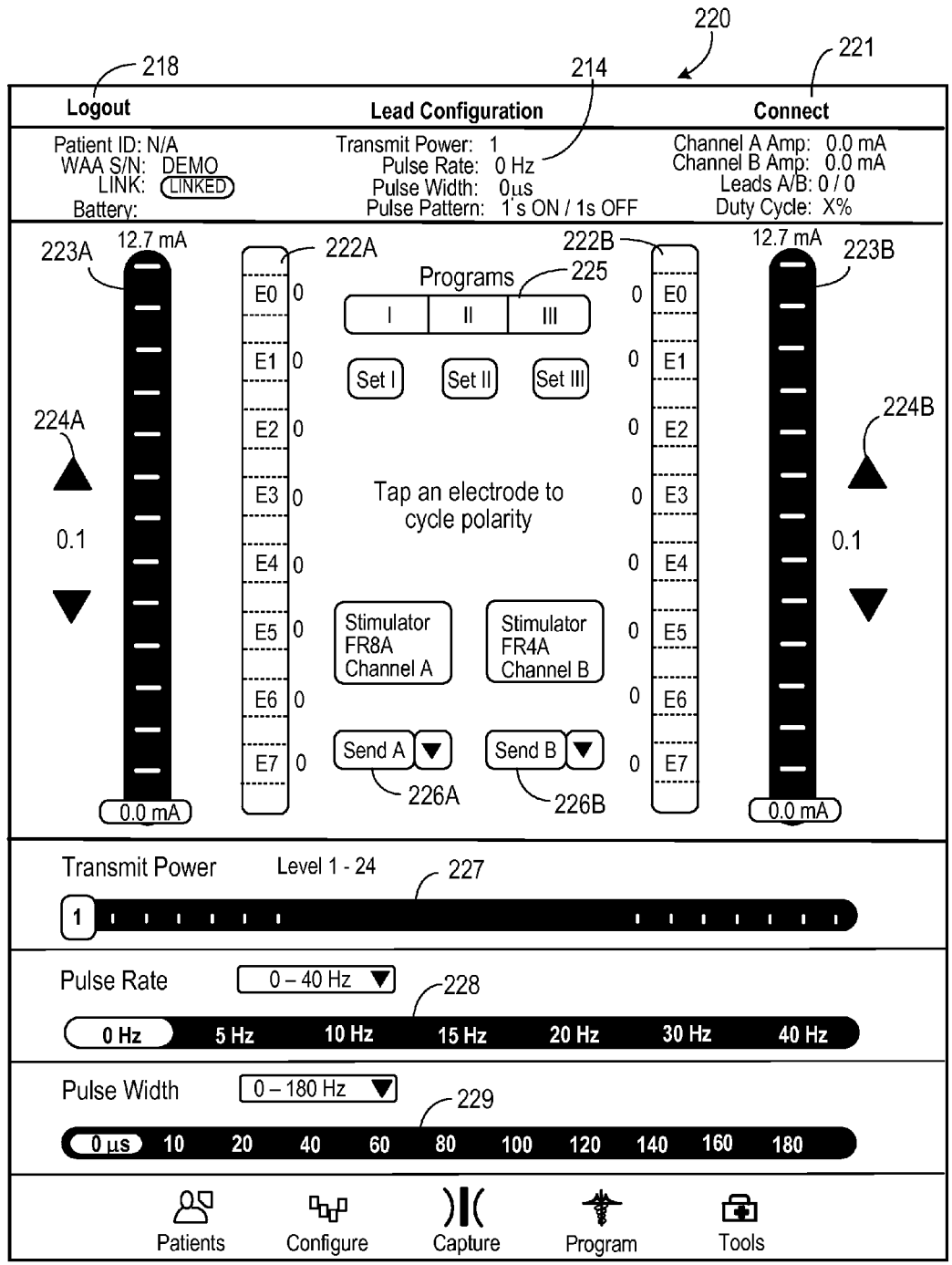

FIG. 2C is an example user interface 220 for the configure view 124, which allows a user to configure the stimulation parameters for the implanted stimulator device. In this illustration, the top panel of user interface 220 includes the same logout tab 218 and patient profile information 214. The top panel may also include connect button 221 to establish a wireless connection with an implanted stimulator device.

As illustrated, the central panel enables a user to configure the polarity and current for each electrode of the implanted stimulator device. A user may tap an electrode icon on electrode arrays 222A and 222B to initiate adjustment of a polarity setting of corresponding electrode. The polarity setting on each array 222A and 222B can be adjusted at the granularity of each electrode. What is more, the central panel also allows the user to configure stimulating current at each electrode pair of the electrode array. For example, user interface 220 may include control bars 223A and 223B, each representing an adjustable range from 0.0 mA to 12.7 mA. In some instances, this adjustable range can be a continuum. In other instances, the adjustable range can include discrete levels. In some of these instances, the discretely adjustable range can be turned up or down through bars 224A and 224B respectively for electrode arrays 222A and 222B.

In some implementations, other than allowing the user to configure the polarity and current setting for each electrode or electrode pair on electrode arrays 223A and 223B, user interface 220 allows the user to choose from pre-existing programs 225, which may include program options I, II, and III, as well as polarity settings options I, II, and III. Each program option may include pre-set polarity settings for each electrode. Each program option can also include pre-set pulse parameters such as transmit power, pulse rate, and pulse width. Each polarity settings option may include the polarity configuration for each electrode of the multi-electrode stimulator device. Transmission buttons 226A and 226B allow information encoding a chosen setting to be sent to the connected implantable device and effectuate the chosen setting.

The bottom panel of user interface 220 includes control bar 227 for configuring transmit power, control bar 228 for configuring pulse rate, and control bar 229 for controlling pulse width. As illustrated, the transmit power can be configured within an adjustable range, for example, from level 1 to level 24. Each level may represent a particular amount of transmit power with level 1 being the lowest and level 24 being the highest power. The levels may be on a linear scale or a logarithmic scale. In some instances, the levels may range from 1 W to 60 W. The transmit power may refer to the electric power being transmitted over a wireless connection from the controller device to the implanted stimulator device, and may directly impact or result in the pulse amplitude applied at the electrodes. The pulse rate may be configured within an adjustable range from 0 Hz to 40 Hz. The pulse width may be configured within an adjustable range from 0 to 180 µs. As illustrated, the adjustable ranges of transmit power, pulse rate, and pulse width can be configured in discrete steps. In other cases, these parameters may be implemented on a continuum range. Some implementations may opt to have a configurable pulse amplitude representing the actual pulse amplitude being applied at a particular electrode. In such implementations, the pulse amplitude configuration option may be provided in lieu of the transmit power configuration option (e.g., shown in control bar 227).

Figure 2D:
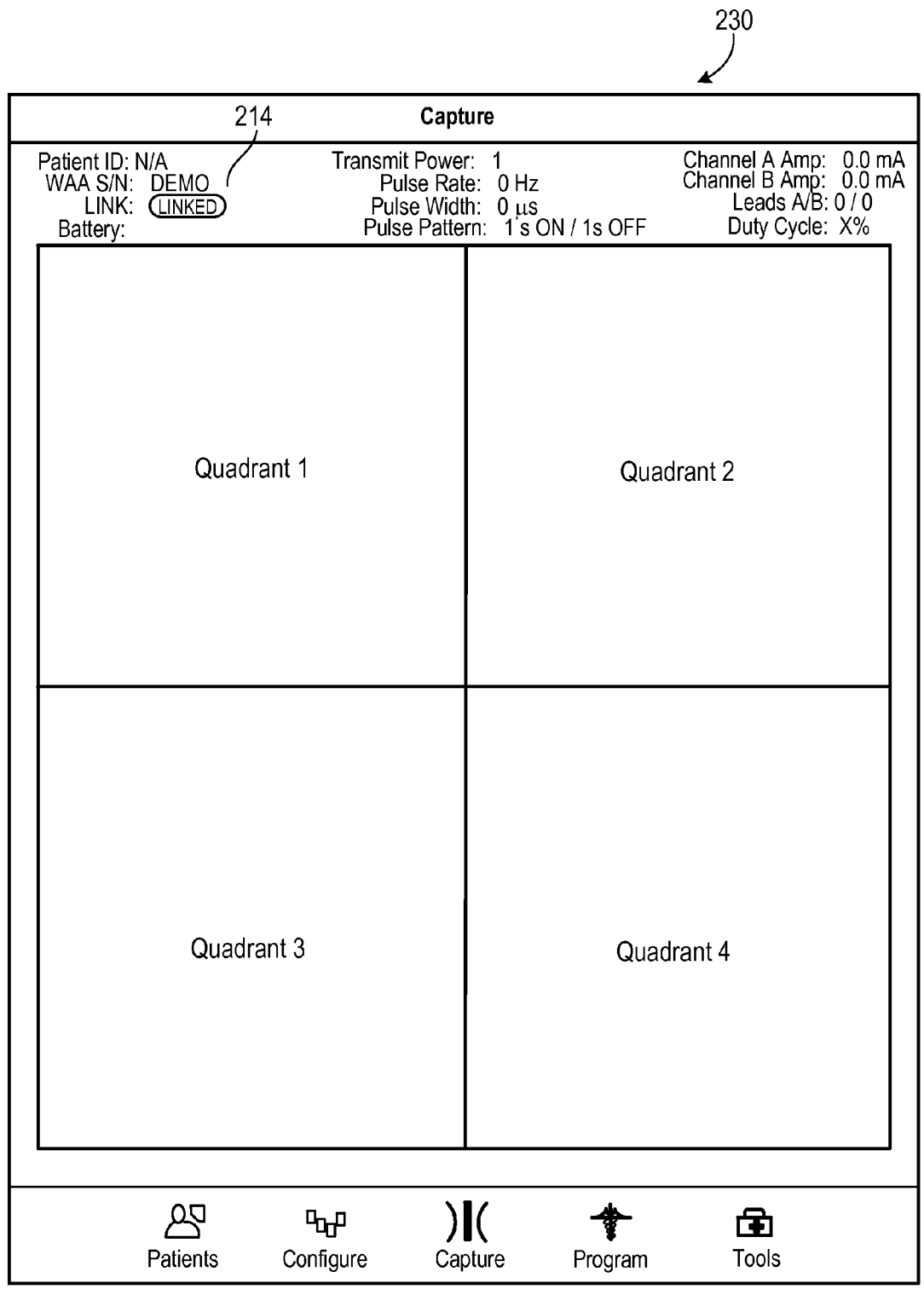

FIG. 2D shows example user interface 230 for the map view 126, which can be used to capture user positioning information for the implanted stimulator device as a media file element. In this illustration, the top panel of user interface 230 includes the same patient profile information 214. The captured user positioning information may be placed in any of up to four quadrants. In some implementations, the captured user positioning information may include fluoroscopic image(s) of the implantation site, for example, showing a radio-opaque implantable stimulator underneath the skin. In these implementations, the fluoroscopic image(s) may include a X-ray image that functions as a reference image being presented in one of the four quadrants. In these implementations, the fluoroscopic image(s) may be taken by a clinician (e.g., a practicing nurse or caregiver) at a clinic. During an adjustment session, the user may take photos from a camera on, for example, an iPad device. The photos may be presented in other quadrants to provide visual guidance during placement of a MFS device relative to the implanted stimulator device underneath the skin. In some implementations, the user or the clinician may take a photo of the body area where the implantable stimulator was placed within the body. The photo taken may be displayed at one of the quadrants, for example, as a reference view. In these implementations, subsequent photos taken from different angles may be displayed at the remaining quadrants. In combination with the reference view, these photos may allow the user to obtain a rather panoramic view of the body area where stimulation parameters are being adjusted. Similarly, subsequent photos may be compared to the reference view to allow the user to replicate camera positioning or adjustment of parameters. Thus, the four illustrated quadrants may allow the user to take photos using, for example, an iPad, to quickly record important information and store such information.

In some instances, the photos of the implantation site are correlated with the fluoroscopic or other imaging technology image showing the implanted stimulator device in the area of the implantation site. In these instances, the photos may represent a stereo view of the implantation site to guide the placement of the controller device. Here, the correlation may provide navigational guidance as to an improved positioning of the MFS device for better coupling when establishing a wireless connection between an MFS device and the implanted stimulator device.

Figure 2E:
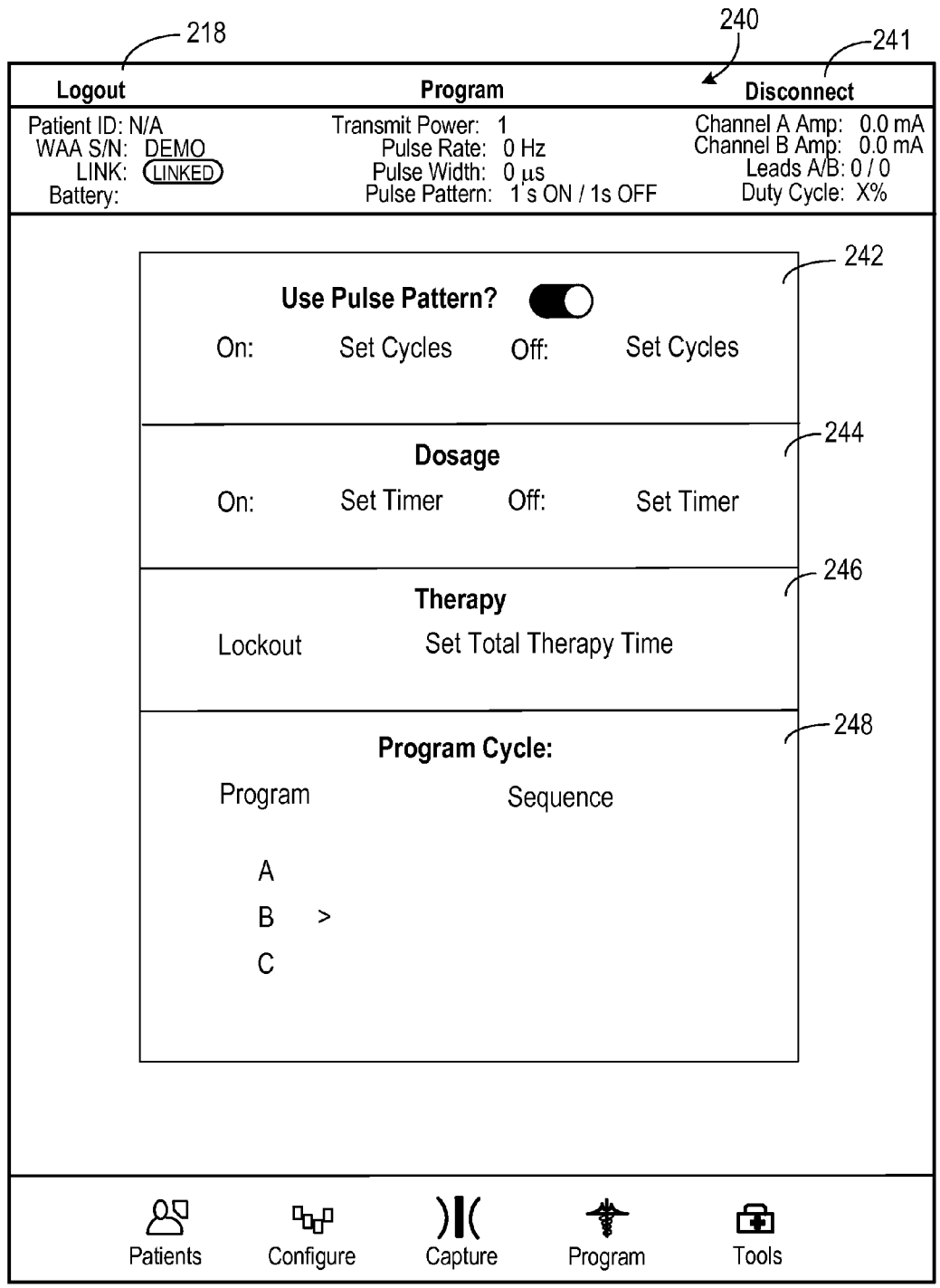

FIG. 2E shows an example user interface 240 for the program view 128, which may be used by a user to set up a stimulation program on an implanted stimulator device. In this illustration, the top panel of user interface 240 includes the same logout tab 218 and patient profile information 214. The top panel may also include a disconnect button 241 to deactivate a wireless connection with an implanted stimulator device. The main panel of user interface 240 may include (i) pulse pattern panel 242 to determine whether to set a pulse pattern for the stimulating currents, (ii) dosage panel 244 to determine whether to use a timer to track dosage, (iii) therapy panel 246 to set a lockout time in accordance with configurable total therapy time, and (iv) program cycle pattern 248 to set up a treatment sequence. For context, a treatment sequence is a concatenation of one or more programs of pulse patterns. A lockout time is a period above which the controller device will be locked so that no more stimulation may be accumulated.

Figure 2F:
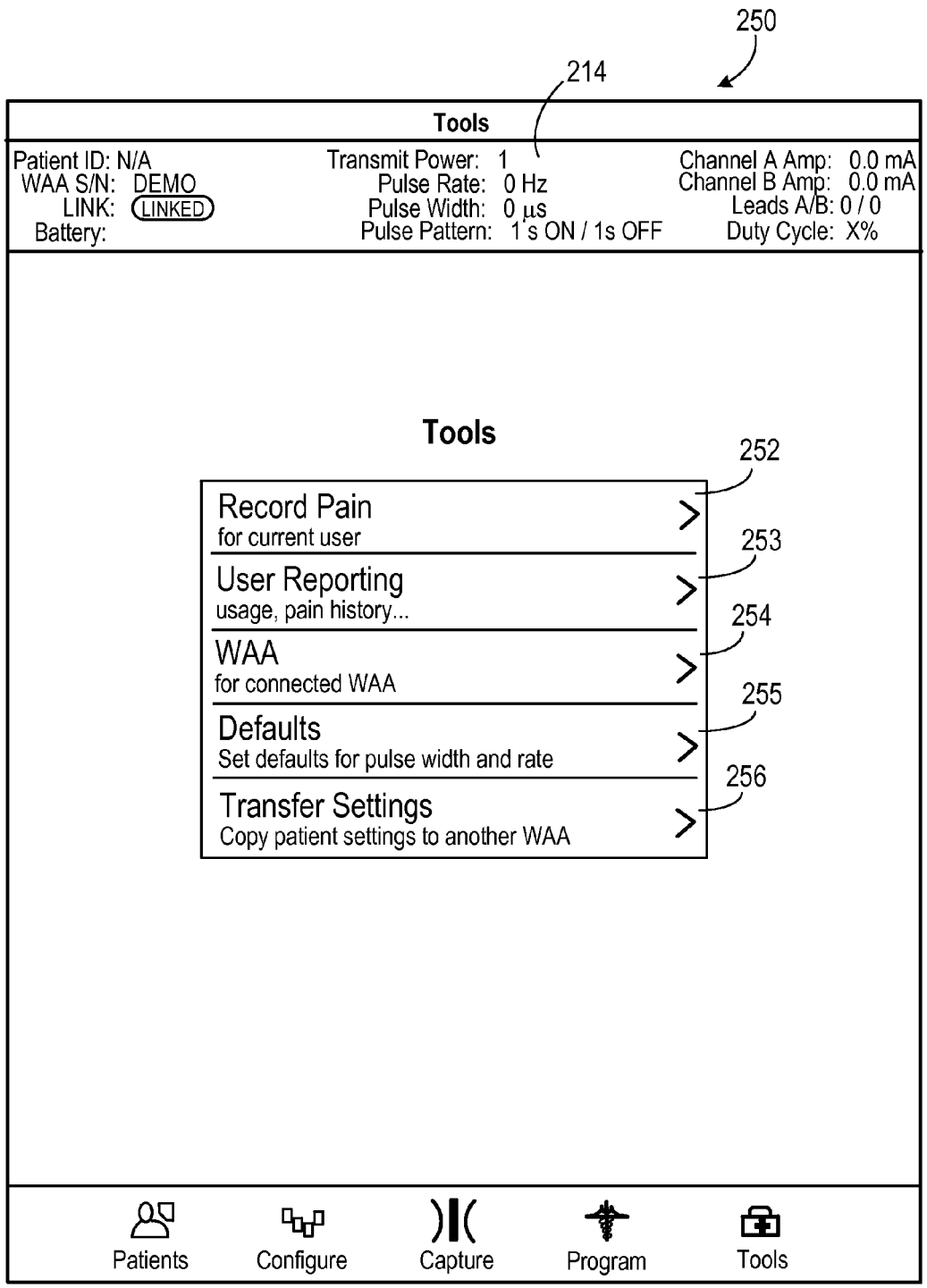

FIG. 2F shows an example user interface 250 for the tools view 130, which displays tools for a user to configure stimulation parameters. In this illustration, the top panel of user interface 250 includes the same patient profile information 214. The main tools panel includes a menu including menu option 252 for recording pain, a menu option 253 for user reporting, a menu option 254 for details of the wearable antenna assembly (WAA), a menu option 255 for Defaults, and a menu option 256 for transfer settings. Menu option 252 allows a user to record pain levels during parameter adjustment to help the user determining an improved parameter setting. Menu option 253 allows a user to submit recorded pain history as well as usage data showing how much and how often the stimulator device has been used. Notably, menu option 252 may record an adjustment in a configuration option made by the user that results in an improved quantitative index of pain. When recording the adjustment in the configuration option, adjustment in a pulse parameter or a polarity setting may be recorded. In particular, the recorded adjustment in the configuration option can be leveraged when generating a recommended configuration setting. In other words, the at least one recommended configuration option may be generated faster than otherwise in the absence of the recorded adjustment. The recorded adjustment may incorporate the corresponding user-reported pain relief at this configuration option. Menu option 255 allows a user to set default stimulation parameter for a connected stimulator device. Menu option 256 allows a user to copy patient settings to another WAA. The WAA is the external transmitter unit that transmits power and instructions to the implanted stimulators. In some implementations, the WAA is the MFS device that the programming unit communicates with. If the user interchanges a WAA for a different serialized WAA unit, the application will facilitate the transfer of the configurations from one WAA to the next on request. As explained above in association with FIG. 1B, the WAA can be an MFS device or a relay module.

Figure 3:
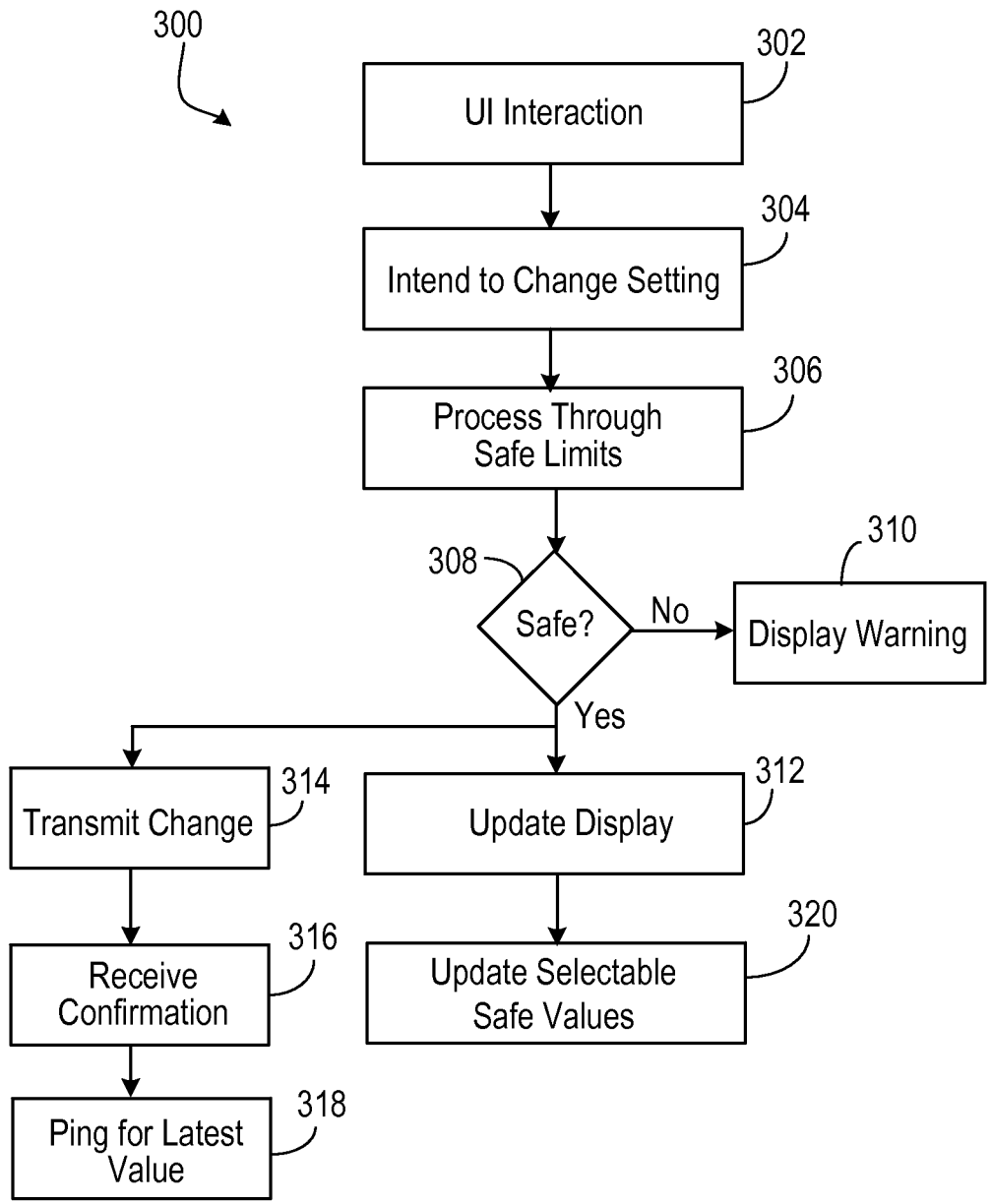
FIG. 3 is a flow chart of a process to configure stimulation settings of the implanted simulator device.

FIG. 3 is a flow chart 300 for a user interface module to configure stimulation settings of the implanted simulator device. Initially, through a user interface (UI) interaction (302), a user announces an intent to change settings for a stimulation device (304). In some instances, the announcement may be made by the configure button to invoke a configuration user interface 220, as illustrated in FIG. 2C. Subsequently, the control program may impose safety limits (306). In some instances, the safety limits may be a predetermined threshold amount and documented in the database 101. In some instances, the safety limits may be determined based on a combination of polarity settings as well as pulse parameters (including pulse rate, pulse width, and transmit power). The safety limits may be determined by fuzzy logic or neural network based weighting algorithms to factor in various empirical data from past recorded data of patient experience. For example, a user may be particularly sensitive to certain combination of polarity settings and pulse parameters. Such combinations, or combinations close to such combinations, may be avoided as a pre-caution. In these instances, neural network based weighting algorithm can provide judiciously chosen safety limits (e.g., on pulse rates) based on a patient's diagnosis and past experience.

If the parameter changes are deemed unsafe, the controller program may display a warning message (310). In some instances, the warning message may include a pop-up window. In some instances, the warning message may include an audio component, such as an alarm sound.

If the parameter changes are determined to be safe, the controller program may proceed by transmitting changes to the MFS (314), which may communicate with the implanted stimulator device as appropriate. The transmitted data may be received by the MFS and, in a handshake manner, the MFS may transmit a confirmation message back to the external controller. The confirmation message may be received and can serve as a success indication of the parameter transmit (316). In some instances, the external controller may ping the MFS for latest data encoding polarity settings and pulse parameters (including pulse rate, pulse width, and transmit power) (318). Thereafter, the controller program may update a display (312), for example, by showing an updated user profile 214 to reflect the latest parameters obtained. The controller program may also update the selectable safety values (320). In some implementations, the selectable safety values may affect the choices for pulse pattern, dosage, and lockout time, as illustrated in FIG. 2E.

Some implementations can allow users to navigate the wider range of choices. As noted in FIG. 2C, the introduction of polarity settings at the granularity of each electrode greatly expands the possibility of the configuration space. For example, there are 16 possible polarity settings in addition to three continuum ranges for RF power/pulse amplitude, pulse rate, and pulse width. To navigate the user through this universe of configuration space, software algorithms are incorporated in these implementations to aid users in selecting configurations of the stimulation parameters. In particular, some implementations record patient feedback for each particular combination of polarity settings and pulse parameters. The recorded patient feedback can form an expert knowledge database to predict later configurations. The later configurations may apply to the same patient, or patients in a comparable group as classified by age, gender, target nerve or tissue, depth of implantation, or type of implanted stimulator devices. For example, a learning engine may be trained based on training data from a group of users that includes, for example, stimulation parameters and resulting pain indexes as well as other variables such as patient age, patient gender, target nerve, anatomic orientation, depth' of implantation, type of implanted stimulator devices, duration of therapy, and/or time of day. The trained learning engine may then suggest to a given patient one or more initial stimulation parameters, such as pulse amplitude, pulse width, pulse rate, and/or polarity based on, for instance, that given patient's age, gender, target nerve, depth of implantation, type of implanted stimulator devices, duration of therapy, time of day, and/or non-suggested stimulation parameters. As that given patient conducts therapy, the patient may provide feedback about his or her pain and adjust the stimulation parameters, and the learning engine may develop a profile specific that to that user and provide suggested stimulation parameters for future sessions.

Figure 4A:
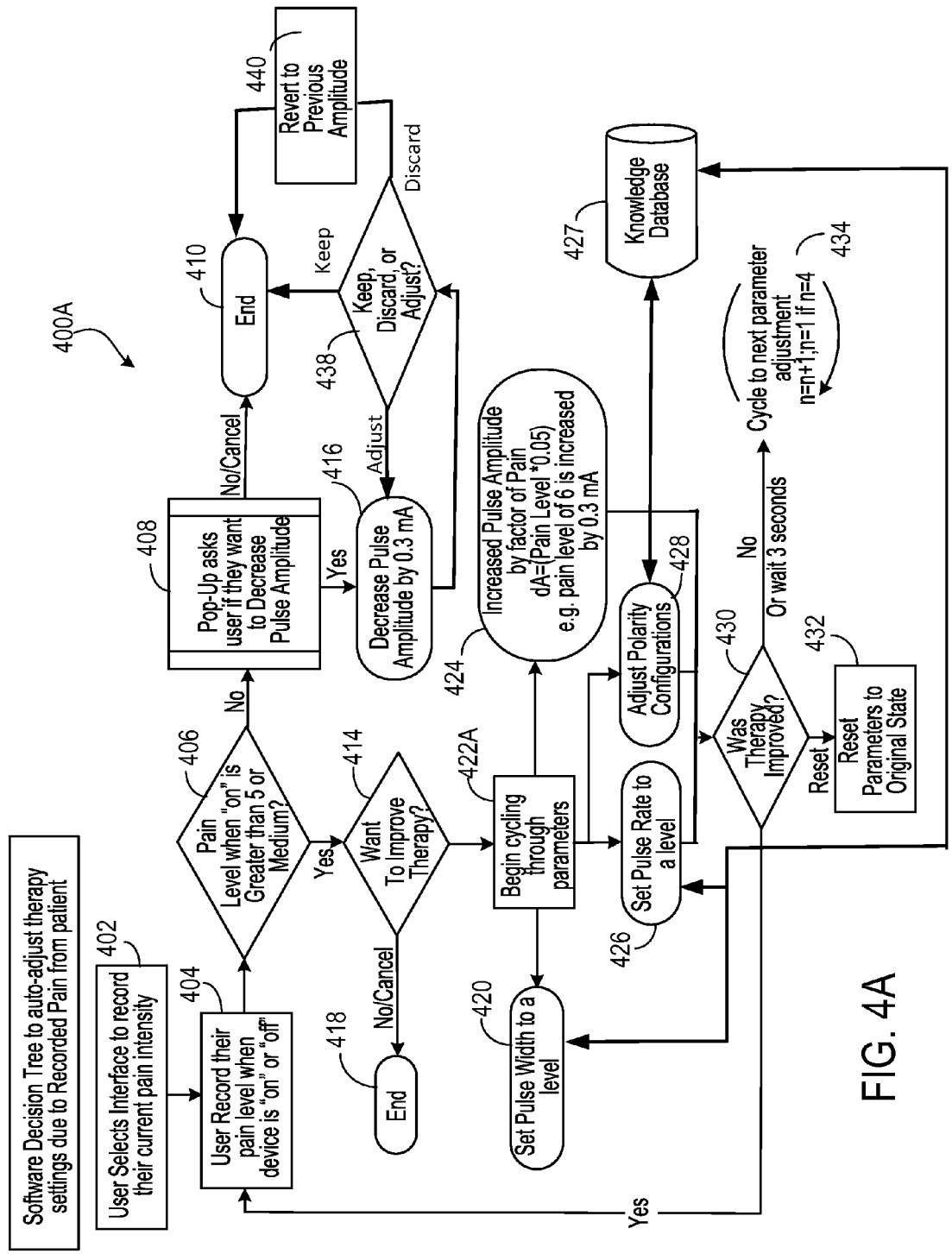
FIGS. 4A and 4B show example software decision trees to auto-adjust therapy settings based on recorded pain.
Figure 4B:
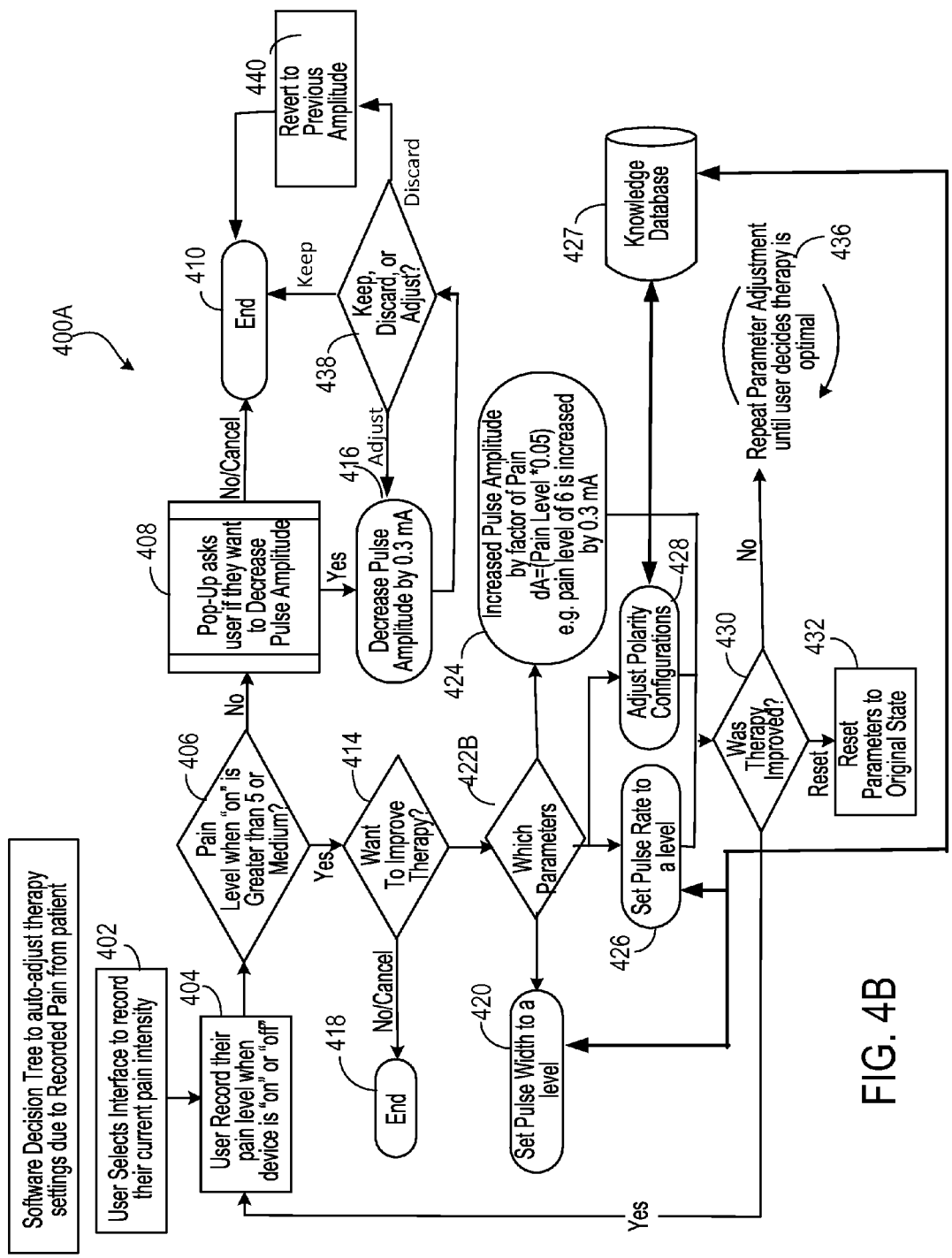

FIGS. 4A and 4B show example software decision trees 400A and 400B to auto-adjust therapy settings based on user recorded pain. In 400A, initially, a user may select an interface to record his/her current pain intensity (402). The selection may be through, for example, menu option 252 at example user interface 250. When the selection is made, the user may then record their pain level. For the purpose of running through the two auto-configurations, the state of 'off' has no effect on the algorithm of auto-adjustment. Thus recording can be made when the implanted stimulator device is "on" or "off" (404). When the stimulator device is "on," a first determination is made regarding whether the pain level is greater than 5 or medium (406). In some instances, the determination is based on user input.

If the pain level is greater than 5 or medium, a determination is made regarding whether to improve therapy (414). In one branch, the user may indicate whether the user may want to improve therapy (414) by changing pulse parameters or polarity settings. If the user does not wish to improve therapy, the process may conclude (418). If the user's desire is to improve therapy, then the process begins cycling through the parameters to be adjusted (422A). In one branch, the process may adjust polarity configurations in an effort to fine tune the effect of stimulation (428). The adjustment may be initiated from a recommendation that is derived based on a knowledge database/learning engine 427. For example, the suggested polarity configuration can be determined by the knowledge database/learning engine 427 based on parameters such as patient's age, gender, target nerve, depth of implantation, type of implanted stimulator device, duration of therapy, time of day, non-suggested stimulation parameters, and/or historical stimulation parameters and resulting pain.

In yet another branch, the process may proceed to set pulse rate to a level (426). In still yet another branch, the process may proceed to set pulse width to a level (420). In another branch, the process may increase pulse amplitude by a particular amount (424). The amount may scale with the reported pain level, for example, in the amount of Pain Level×0.05. In these latter branches, the pulse rate or pulse width may be randomly selected from a sub-range of values from the full range of the values. The subrange may be selected by the knowledge database/learning engine 427 based on parameters such as patient's age, gender, target nerve, depth of implantation, type of implanted stimulator device, duration of therapy, time of day, non-suggested stimulation parameters, and/or historical stimulation parameters and resulting pain. By randomly selecting values for pulse width and pulse rate, the patient is more likely to notice a difference in treatment than if values for these parameters were sequentially changed.

After a given one of the stimulation parameters are adjusted, a determination is made as to whether therapy was improved (430). If the user indicates that the therapy has improved, the process may loop back to ask the user to record pain relief (404). If the user indicates that the therapy has not improved, or no user feedback is received within 3 seconds, the process may cycle to next parameter adjustment (434). For example, the process may cycle from pulse width adjustment to pulse rate adjustment (or vice versa). In this manner, the process 400A adjusts one parameter sequentially at a time, asking the patient if therapy has improved after each adjustment. If not, or after a short period of time, the process updates the next parameter and again asks the patient if therapy has improved.

The determination (430) also provides a third option for the user to choose—the reset. If chosen, the program may enter the reset branch in which stimulation parameters, including polarity settings, are reset to original state before adjustments (432). The reset branch reverts the stimulation configurations (including pulse parameters and electrode polarity settings) back to the original state prior to user adjustment.

When the user has already selected a therapy program and has received pain relief from the therapy program, a pop-up window may be displayed to ask the user if the user wants to decrease pulse amplitude (408) if, for example, the pain level is not greater than, for example, 5 or medium. In some cases, the user may receive relief from the treatment, but the treatment may be uncomfortable if the pulse amplitude is high. If the user does not want to decrease the amplitude, the decision tree may conclude (410). If the user indicates that the user wants to decrease the pulse amplitude, the process 400A decreases pulse amplitude as executed on the implanted stimulator device by a certain amount (e.g., by 0.3 mA) (416). A determination is then made regarding if therapy is still providing sufficient pain relief even at the decreased pulse amplitude such that the user may keep the adjusted pulse amplitude, discard the adjusted pulse amplitude, or further adjust the pulse amplitude (438). If the therapy is still providing sufficient pain relief and the patient is no longer uncomfortable (or otherwise decides that the current pulse amplitude is satisfactory), the user may decide to keep the adjusted pulse amplitude and process 400A may conclude (410). When the therapy is still providing sufficient pain relief and the user still wishes to refine the pulse amplitude (or the adjusted pulse amplitude remains an uncomfortable choice), the decreased pulse amplitude may be further adjusted (416). If the therapy is no longer providing sufficient pain relief, the user may decide to revert the pulse amplitude to the previously set amplitude and the process 400A may do so (440) before concluding the adjustment (410).

Process 400B, as depicted in FIG. 4B, largely tracks process 400A from FIG. 4A. The main difference between process 400A and 400B is that when the user indicates that the user would like to improve therapy, the user is asked which parameter to adjust and then the process continues to adjust just that parameter. Accordingly, if the user's desire is to improve therapy, then the user is prompted to select a parameter to adjust (422B). For example, the user can select the pulse width, pulse rate, pulse amplitude, or polarity. The selected parameter is then adjusted (420, 426, 428, or 424), for example, in the manner described with respect to FIG. 4A and the user is asked if therapy is improved (430). If not, then the selected parameter is adjusted until the user decides therapy has improved (434). The other actions of process 400B occur as described with respect to the corresponding actions in process 400A.

Figure 5A:
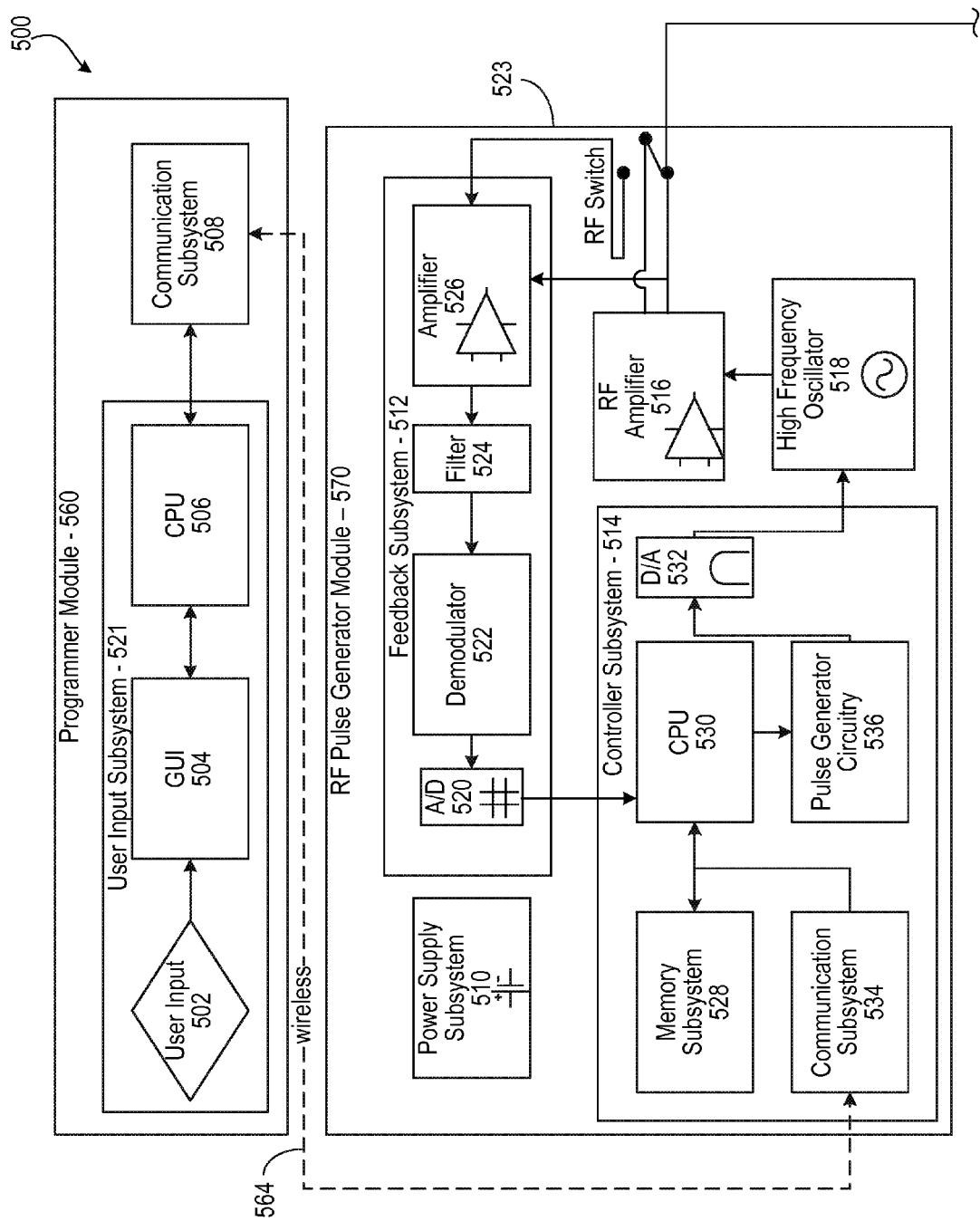
FIGS. 5A and 5B are detailed diagrams of an example of a wireless neural stimulation system.
Figure 5B:
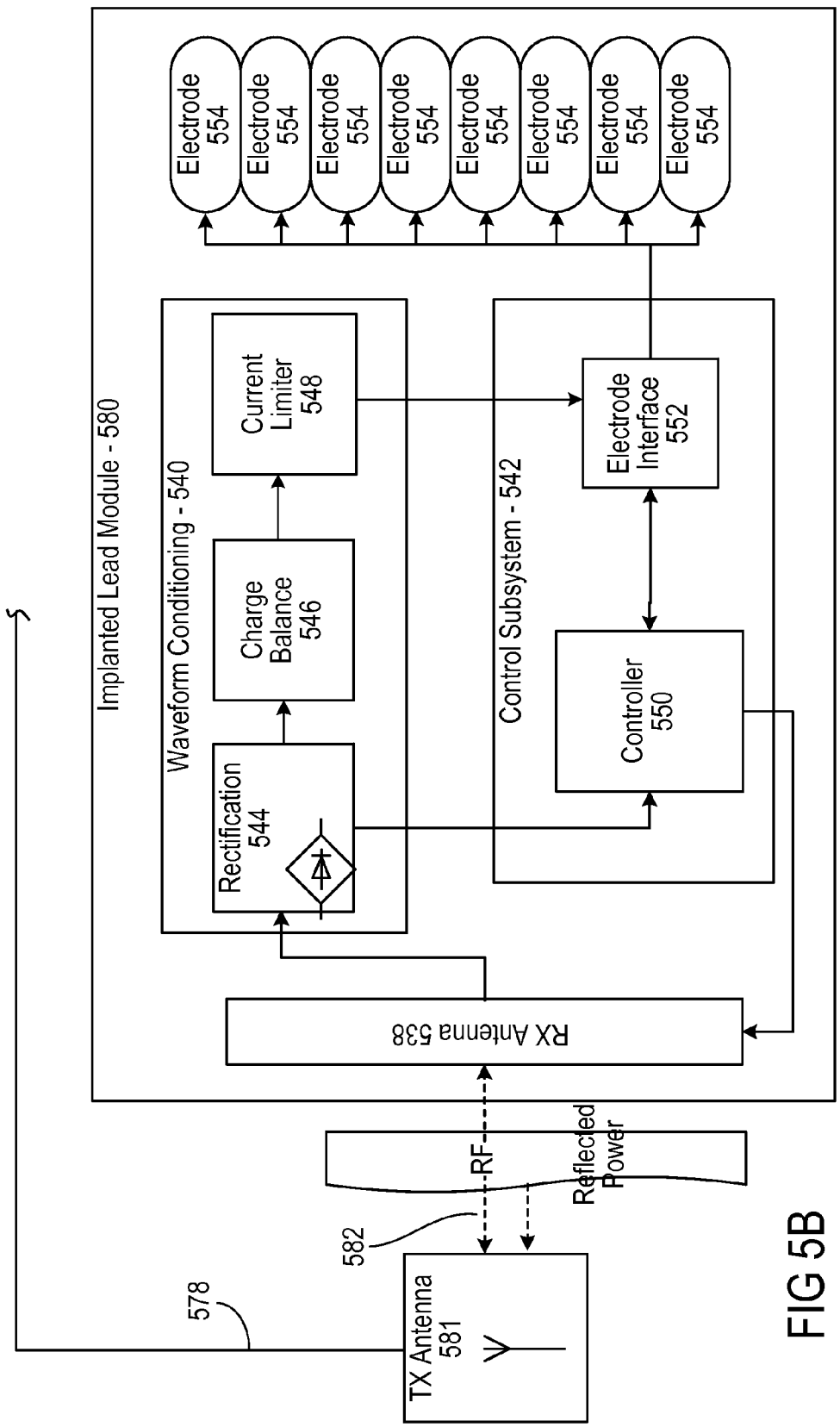

FIG. 5 depicts a detailed diagram 500 of an example of a neural stimulation system including programming module 560, RF pulse generator module 570, and implantable neural stimulator module 580. Programming module 560 and RF pulse generator module 570 may respectively correspond to the mobile computing device and MFS discussed above in association with FIG. 1. Implantable neural stimulator module 580 may correspond to the implanted stimulator device discussed above in association with FIG. 1.

As depicted, the programming module 560 may comprise user input system 502 and communication subsystem 508. The user input system 521 may allow various parameter settings to be adjusted (in some cases, in an open loop fashion) by the user in the form of instruction sets. The communication subsystem 508 may transmit these instruction sets (and other information) via the wireless connection 564, such as Bluetooth or Wi-Fi, to the RF pulse generator module 570, as well as receive data from module 570.

For instance, the programmer module 560, which can be utilized for multiple users, such as a patient's control unit or clinician's programmer unit, can be used to send stimulation parameters to the RF pulse generator module 560. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

Stimulation Parameter Table 1
Pulse Amplitude: 0 to 20 mA
Pulse Frequency: 0 to 2000 Hz
Pulse Width: 0 to 2 ms The implantable neural stimulator module 580 or RF pulse generator module 570 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 560 may be functionally a smart device and associated application. The smart device hardware may include a CPU 506 and be used as a vehicle to handle touchscreen input on a graphical user interface (GUI) 504, for processing and storing data.

The RF pulse generator module 506 may be connected via wired connection 578 to an external TX antenna 510. Alternatively, both the antenna and the RF pulse generator are located subcutaneously (not shown).

The signals sent by RF pulse generator module 570 to the implanted stimulator module 580 may include both power and parameter-setting attributes in regards to stimulus waveform, amplitude, pulse width, and frequency. The RF pulse generator module 570 can also function as a wireless receiving unit that receives feedback signals from the implanted stimulator module 580. To that end, the RF pulse generator module 570 may contain microelectronics or other circuitry to handle the generation of the signals transmitted to the implanted stimulator module 580 as well as handle feedback signals, such as those from the implanted stimulator module 580. For example, the RF pulse generator module 570 may comprise controller subsystem 514, high-frequency oscillator 518, RF amplifier 516, a RF switch, and a feedback subsystem 512.

The controller subsystem 514 may include a CPU 530 to handle data processing, a memory subsystem 528 such as a local memory, communication subsystem 534 to communicate with programmer module 560 (including receiving stimulation parameters from programmer module), pulse generator circuitry 570, and digital/analog (D/A) converters 532.

The controller subsystem 514 may be used by the patient and/or the clinician to control the stimulation parameter settings (for example, by controlling the parameters of the signal sent from RF pulse generator module 570 to neural stimulator module 580). These parameter settings can affect, for example, the power, current level, or shape of the one or more electrical pulses. The programming of the stimulation parameters can be performed using the programming module 560, as described above, to set the repetition rate, pulse width, amplitude, and waveform that will be transmitted by RF energy to the receive (RX) antenna 538, typically a dipole antenna (although other types may be used), in the wireless implanted neural stimulator module 514. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 514 may store received parameter settings in the local memory subsystem 528, until the parameter settings are modified by new input data received from the programming module 560. The CPU 506 may use the parameters stored in the local memory to control the pulse generator circuitry 536 to generate a stimulus waveform that is modulated by a high frequency oscillator 518 in the range from 300 MHz to 8 GHz. The resulting RF signal may then be amplified by RF amplifier 526 and then sent through an RF switch 523 to the TX antenna 581 to reach through depths of tissue to the RX antenna 538.

In some implementations, the RF signal sent by TX antenna 581 may simply be a power transmission signal used by stimulator module 580 to generate electric pulses. In other implementations, a telemetry signal may also be transmitted to the stimulator module 580 to send instructions about the various operations of the stimulator module 580. The telemetry signal may be sent by the modulation of the carrier signal (through the skin if external, or through other body tissues if the pulse generator module 570 is implanted subcutaneously). The telemetry signal is used to modulate the carrier signal (a high frequency signal) that is coupled onto the implanted antenna(s) 538 and does not interfere with the input received on the same stimulator to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 523 may be a multipurpose device such as a dual directional coupler, which passes the relatively high amplitude, extremely short duration RF pulse to the TX antenna 581 with minimal insertion loss while simultaneously providing two low-level outputs to feedback subsystem 512; one output delivers a forward power signal to the feedback subsystem 512, where the forward power signal is an attenuated version of the RF pulse sent to the TX antenna 581, and the other output delivers a reverse power signal to a different port of the feedback subsystem 512, where reverse power is an attenuated version of the reflected RF energy from the TX Antenna 581.

During the on-cycle time (when an RF signal is being transmitted to stimulator 580), the RF switch 523 is set to send the forward power signal to feedback subsystem. During the off-cycle time (when an RF signal is not being transmitted to the stimulator module 580), the RF switch 523 can change to a receiving mode in which the reflected RF energy and/or RF signals from the stimulator module 580 are received to be analyzed in the feedback subsystem 512.

The feedback subsystem 512 of the RF pulse generator module 570 may include reception circuitry to receive and extract telemetry or other feedback signals from the stimulator 580 and/or reflected RF energy from the signal sent by TX antenna 581. The feedback subsystem may include an amplifier 526, a filter 524, a demodulator 522, and an A/D converter 520.

The feedback subsystem 512 receives the forward power signal and converts this high-frequency AC signal to a DC level that can be sampled and sent to the controller subsystem 514. In this way the characteristics of the generated RF pulse can be compared to a reference signal within the controller subsystem 514. If a disparity (error) exists in any parameter, the controller subsystem 514 can adjust the output to the RF pulse generator 570. The nature of the adjustment can be, for example, proportional to the computed error. The controller subsystem 514 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 581 has perfectly matched impedance to the tissue that it contacts, the electromagnetic waves generated from the RF pulse generator 570 pass unimpeded from the TX antenna 581 into the body tissue. However, in real-world applications a large degree of variability may exist in the body types of users, types of clothing worn, and positioning of the antenna 581 relative to the body surface. Since the impedance of the antenna 581 depends on the relative permittivity of the underlying tissue and any intervening materials, and also depends on the overall separation distance of the antenna from the skin, in any given application there can be an impedance mismatch at the interface of the TX antenna 581 with the body surface. When such a mismatch occurs, the electromagnetic waves sent from the RF pulse generator 570 are partially reflected at this interface, and this reflected energy propagates backward through the antenna feed.

The dual directional coupler RF switch 523 may prevent the reflected RF energy propagating back into the amplifier 526, and may attenuate this reflected RF signal and send the attenuated signal as the reverse power signal to the feedback subsystem 512. The feedback subsystem 512 can convert this high-frequency AC signal to a DC level that can be sampled and sent to the controller subsystem 514. The controller subsystem 514 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 514 can measure the reflected-power ratio in real time, and according to preset thresholds for this measurement, the controller subsystem 514 can modify the level of RF power generated by the RF pulse generator 570. For example, for a moderate degree of reflected power the course of action can be for the controller subsystem 514 to increase the amplitude of RF power sent to the TX antenna 581, as would be needed to compensate for slightly non-optimum but acceptable TX antenna coupling to the body. For higher ratios of reflected power, the course of action can be to prevent operation of the RF pulse generator 570 and set a fault code to indicate that the TX antenna 581 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless neural stimulator and thus cannot deliver therapy to the user.

The controller 542 of the stimulator 580 may transmit informational signals, such as a telemetry signal, through the antenna 538 to communicate with the RF pulse generator module 570 during its receive cycle. For example, the telemetry signal from the stimulator 580 may be coupled to the modulated signal on the dipole antenna(s) 538, during the on and off state of the transistor circuit to enable or disable a waveform that produces the corresponding RF bursts necessary to transmit to the external (or remotely implanted) pulse generator module 570. The antenna(s) 538 may be connected to electrodes 554 in contact with tissue to provide a return path for the transmitted signal. An A/D (not shown) converter can be used to transfer stored data to a serialized pattern that can be transmitted on the pulse modulated signal from the internal antenna(s) 538 of the neural stimulator.

A telemetry signal from the implanted wireless neural stimulator module 580 may include stimulus parameters such as the power or the amplitude of the current that is delivered to the tissue from the electrodes. The feedback signal can be transmitted to the RF pulse generator module 570 to indicate the strength of the stimulus at the nerve bundle by means of coupling the signal to the implanted RX antenna 538, which radiates the telemetry signal to the external (or remotely implanted) RF pulse generator module 570. The feedback signal can include either or both an analog and digital telemetry pulse modulated carrier signal. Data such as stimulation pulse parameters and measured characteristics of stimulator performance can be stored in an internal memory device within the implanted neural stimulator 580, and sent on the telemetry signal. The frequency of the carrier signal may be in the range of at 300 MHz to 8 GHz.

In the feedback subsystem 512, the telemetry signal can be down modulated using demodulator 522 and digitized by being processed through an analog to digital (A/D) converter 520. The digital telemetry signal may then be routed to a CPU 530 with embedded code, with the option to reprogram, to translate the signal into a corresponding current measurement in the tissue based on the amplitude of the received signal. The CPU 530 of the controller subsystem 514 can compare the reported stimulus parameters to those held in local memory 528 to verify the stimulator(s) 580 delivered the specified stimuli to tissue. For example, if the stimulator reports a lower current than was specified, the power level from the RF pulse generator module 570 can be increased so that the implanted neural stimulator 580 will have more available power for stimulation. The implanted neural stimulator 580 can generate telemetry data in real time, for example, at a rate of 8 kbits per second. All feedback data received from the implanted stimulator module 580 can be logged against time and sampled to be stored for retrieval to a remote monitoring system accessible by the health care professional for trending and statistical correlations.

The sequence of remotely programmable RF signals received by the internal antenna(s) 538 may be conditioned into waveforms that are controlled within the implantable stimulator 580 by the control subsystem 542 and routed to the appropriate electrodes 554 that are placed in proximity to the tissue to be stimulated. For instance, the RF signal transmitted from the RF pulse generator module 570 may be received by RX antenna 538 and processed by circuitry, such as waveform conditioning circuitry 540, within the implanted wireless neural stimulator module 580 to be converted into electrical pulses applied to the electrodes 554 through electrode interface 552. In some implementations, the implanted stimulator 580 contains between two to sixteen electrodes 554.

The waveform conditioning circuitry 540 may include a rectifier 544, which rectifies the signal received by the RX antenna 538. The rectified signal may be fed to the controller 542 for receiving encoded instructions from the RF pulse generator module 570. The rectifier signal may also be fed to a charge balance component 546 that is configured to create one or more electrical pulses based such that the one or more electrical pulses result in a substantially zero net charge at the one or more electrodes (that is, the pulses are charge balanced). The charge-balanced pulses are passed through the current limiter 548 to the electrode interface 552, which applies the pulses to the electrodes 554 as appropriate.

The current limiter 548 insures the current level of the pulses applied to the electrodes 554 is not above a threshold current level. In some implementations, an amplitude (for example, current level, voltage level, or power level) of the received RF pulse directly determines the amplitude of the stimulus. In this case, it may be particularly beneficial to include current limiter 548 to prevent excessive current or charge being delivered through the electrodes, although current limiter 548 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 548 acts as a charge limiter that limits a characteristic (for example, current or duration) of the electrical pulses so that the charge per phase remains below a threshold level (typically, a safe-charge limit).

In the event the implanted wireless neural stimulator 580 receives a "strong" pulse of RF power sufficient to generate a stimulus that would exceed the predetermined safe-charge limit, the current limiter 548 can automatically limit or "clip" the stimulus phase to maintain the total charge of the phase within the safety limit. The current limiter 548 may be a passive current limiting component that cuts the signal to the electrodes 554 once the safe current limit (the threshold current level) is reached. Alternatively, or additionally, the current limiter 548 may communicate with the electrode interface 552 to turn off all electrodes 554 to prevent tissue damaging current levels.

A clipping event may trigger a current limiter feedback control mode. The action of clipping may cause the controller to send a threshold power data signal to the pulse generator 570. The feedback subsystem 512 detects the threshold power signal and demodulates the signal into data that is communicated to the controller subsystem 514. The controller subsystem 514 algorithms may act on this current-limiting condition by specifically reducing the RF power generated by the RF pulse generator, or cutting the power completely. In this way, the pulse generator 570 can reduce the RF power delivered to the body if the implanted wireless neural stimulator 580 reports it is receiving excess RF power.

The controller 550 of the stimulator 580 may communicate with the electrode interface 552 to control various aspects of the electrode setup and pulses applied to the electrodes 554. The electrode interface 552 may act as a multiplex and control the polarity and switching of each of the electrodes 554. For instance, in some implementations, the wireless stimulator 570 has multiple electrodes 554 in contact with tissue, and for a given stimulus the RF pulse generator module 570 can arbitrarily assign one or more electrodes to 1) act as a stimulating electrode, 2) act as a return electrode, or 3) be inactive by communication of assignment sent wirelessly with the parameter instructions, which the controller 550 uses to set electrode interface 552 as appropriate. It may be physiologically advantageous to assign, for example, one or two electrodes as stimulating electrodes and to assign all remaining electrodes as return electrodes.

Also, in some implementations, for a given stimulus pulse, the controller 550 may control the electrode interface 552 to divide the current arbitrarily (or according to instructions from pulse generator module 570) among the designated stimulating electrodes. This control over electrode assignment and current control can be advantageous because in practice the electrodes 554 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 550, on its own or in response to instructions from pulse generator 570, can control electrode interface 552 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 550 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 550 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 550 was configured to match the repetition rate for set B to that of set A, for such a case the controller 550 can specify the relative start times of the stimulus cycles to be coincident in time or to be arbitrarily offset from one another by some delay interval.

In some implementations, the controller 550 can arbitrarily shape the stimulus waveform amplitude, and may do so in response to instructions from pulse generator 570. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 550 can increase or decrease the level of current at any time during the stimulus phase and/or during the charge-balancing phase. Thus, in some implementations, the controller 550 can deliver arbitrarily shaped stimulus waveforms such as a triangular pulse, sinusoidal pulse, or Gaussian pulse for example. Similarly, the charge-balancing phase can be arbitrarily amplitude-shaped, and similarly an anodic pulse (prior to the stimulus phase) may also be amplitude-shaped.

As described above, the stimulator 580 may include a charge-balancing component 546. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm2. In order to avoid the irreversible electrochemical reactions such as pH change, electrode dissolution as well as tissue destruction, no net charge should appear at the electrode-electrolyte interface, and it is generally acceptable to have a charge density less than 30 uC/cm2. Biphasic stimulating current pulses ensure that no net charge appears at the electrode after each stimulation cycle and the electrochemical processes are balanced to prevent net dc currents. Neural stimulator 580 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 546 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless neural stimulator module 580 may create a drive-waveform envelope that follows the envelope of the RF pulse received by the receiving dipole antenna(s) 538. In this case, the RF pulse generator module 570 can directly control the envelope of the drive waveform within the wireless neural stimulator 580, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted neural stimulator 580 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 570, and in others this control may be administered internally by circuitry onboard the wireless stimulator 580, such as controller 550. In the case of onboard control, the amplitude and timing may be specified or modified by data commands delivered from the pulse generator module 570.

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

A number of implementations have been described. Nevertheless, it will be understood that various modifications may be made. Accordingly, other implementations are within the scope of the following claims.

What is claimed is:

1. A computer-assisted method to configure settings on an implanted stimulator device, the method comprising:
   presenting configuration options to a user of the implanted stimulator device, the configuration options comprising stimulation parameters for the implanted stimulator, the stimulation parameters comprising polarity setting such that presenting configuration options to the user of the implanted stimulator device comprises presenting configuration options that include a polarity setting of each electrode of the implanted stimulator device;
   receiving a user specification of the configuration options in response to the presented configuration options;
   receiving user feedback when the user specified configuration options are implemented at the implanted stimulator device, the user feedback comprising a quantitative index of pain resulting from implementing the user specified configuration options on the implanted stimulator device;
   building a user profile for the user based on the user specified configuration options and the user feedback, the user profile including the user specified configuration options as well as the corresponding quantitative index of pain; and
   selecting at least one configuration option based on the user profile when the configuration options are subsequently presented to the user for a later treatment.

2. The method of claim 1, wherein building a user profile for the user comprises building a user profile that includes the polarity setting of each electrode that gives rise to the corresponding quantitative index of pain.

3. The method of claim 2, wherein selecting at least one configuration option further comprises selecting a polarity setting for at least one of the electrodes of the implanted stimulator device.

4. The method of claim 1, wherein the stimulation parameters comprise pulse rate, pulse width, and pulse amplitude such that presenting configuration options comprises presenting configuration options that that include pulse rate, pulse width, and pulse amplitude.

5. The method of claim 4, further comprising: in response to determining that the quantitative index of pain is above a threshold level, prompting the user to change the configuration options.

6. The method of claim 5, wherein prompting the user to change the configuration options comprises presenting at least one configuration option based on the user profile.

7. The method of claim 6, further comprising: increasing, by an amount that is proportional to the quantitative index of pain, a pulse amplitude of stimulation pulses for application at a particular electrode.

8. The method of claim 4, further comprising: in response to determining that the quantitative index of pain is below a threshold level, prompting the user to reduce stimulation.

9. The method of claim 8, wherein prompting the user to reduce stimulation comprises prompting the user to reduce stimulation by decreasing a pulse amplitude of stimulation pulses for application at a particular electrode.

10. The method of claim 1, wherein presenting configuration options further comprises cycling through the each configuration option subject to user adjustment, the configuration options including the polarity setting of each electrode of the implanted stimulator device as well as pulse parameters of stimulation pulses for application at a particular electrode.

11. The method of claim 1, wherein building a user profile further comprises recording an adjustment in a configuration option made by the user that results in an improved quantitative index of pain.

12. The method of claim 11, wherein recording the adjustment in the configuration option includes recording an adjustment in a pulse parameter or a polarity setting.

13. A controller device to configure settings on an implanted stimulator device, the controller device comprising a processor configured to perform the operations of:
   presenting configuration options to a user of the implanted stimulator device, the configuration options comprising stimulation parameters for the implanted stimulator, the stimulation parameters comprising polarity setting such that presenting configuration options to the user of the implanted stimulator device comprises presenting configuration options that include a polarity setting of each electrode of the implanted stimulator device;
   receiving a user specification of the configuration options in response to the presented configuration options;
   receiving user feedback when the user specified configuration options are implemented at the implanted stimulator device, the user feedback comprising a quantitative index of pain resulting from implementing the user specified configuration options on the implanted stimulator device;
   building a user profile for the user based on the user specified configuration options and the user feedback, the user profile including the user specified configuration options as well as the corresponding quantitative index of pain; and
   selecting at least one configuration option based on the user profile when the configuration options are subsequently presented to the user for a later treatment.

14. The controller device of claim 13, wherein building a user profile for the user comprises building a user profile that includes the polarity setting of each electrode that gives rise to the corresponding quantitative index of pain.

15. The controller device of claim 14, wherein selecting at least one configuration option further comprises selecting a polarity setting for at least one of the electrodes of the implanted stimulator device.

16. The controller device of claim 13, wherein the stimulation parameters comprise pulse rate, pulse width, and pulse amplitude such that presenting configuration options comprises presenting configuration options that that include pulse rate, pulse width, and pulse amplitude.

17. The controller device of claim 13, wherein the operations further comprise: in response to determining that the quantitative index of pain is above a threshold level, prompting the user to change the configuration options.

18. The controller device of claim 13, wherein the operations further comprise: further comprising in response to determining that the quantitative index of pain is below a threshold level, prompting the user to reduce stimulation.

* * * * *

UNITED STATES PATENT AND TRADEMARK OFFICE
CERTIFICATE OF CORRECTION

PATENT NO. : 9,731,140 B1  
APPLICATION NO. : 14/952302  
DATED : August 15, 2017  
INVENTOR(S) : Laura Tyler Perryman et al.

Page 1 of 1

It is certified that error appears in the above-identified patent and that said Letters Patent is hereby corrected as shown below:

In the Claims

In Claim 4, Column 20, Line 50, delete "that that" and insert -- that --, therefor.

In Claim 16, Column 22, Line 23 (approx.), delete "that that" and insert -- that --, therefor.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*